United States Patent
Stempfle et al.

(10) Patent No.: US 9,675,753 B2
(45) Date of Patent: Jun. 13, 2017

(54) SAFE DRUG DELIVERY SYSTEM

(75) Inventors: Julius Stempfle, Suwanee, GA (US);
Chang-Jung Lee, Alpharetta, GA (US);
William D. Arthur, III, Santa Rosa Beach, FL (US)

(73) Assignee: Atlanta Biomedical Corp., Suwanee, GA (US)

(*) Notice: Subject to any disclaimer, the term of this patent is extended or adjusted under 35 U.S.C. 154(b) by 843 days.

(21) Appl. No.: 13/448,047

(22) Filed: Apr. 16, 2012

(65) Prior Publication Data

US 2013/0274669 A1    Oct. 17, 2013

(51) Int. Cl.
*A61M 5/142* (2006.01)
*A61M 5/145* (2006.01)

(52) U.S. Cl.
CPC ....... *A61M 5/1456* (2013.01); *A61M 2205/52* (2013.01); *A61M 2205/6009* (2013.01); *A61M 2205/6018* (2013.01); *A61M 2205/6054* (2013.01); *A61M 2205/6063* (2013.01)

(58) Field of Classification Search
CPC ......... A61M 2005/14296; A61M 2005/14208; A61M 5/1456; A61M 2205/6018; A61M 2205/6009; G06F 19/325; G06F 19/3412; G06F 19/3406

USPC ............... 604/65–67, 131, 890.1; 705/2, 3
See application file for complete search history.

(56) References Cited

U.S. PATENT DOCUMENTS

| | | | |
|---|---|---|---|
| 6,356,789 B1 * | 3/2002 | Hinssen et al. | 607/60 |
| 6,938,165 B2 * | 8/2005 | Inoue et al. | 713/193 |
| 7,048,193 B2 | 5/2006 | Tsukada et al. | |
| 7,686,789 B2 * | 3/2010 | Nemoto et al. | 604/246 |
| 7,898,416 B2 * | 3/2011 | Fago | A61M 5/007 235/385 |
| 2002/0038392 A1 * | 3/2002 | De La Huerga | A61M 5/14212 710/8 |
| 2005/0144043 A1 * | 6/2005 | Holland et al. | 705/3 |
| 2009/0043253 A1 * | 2/2009 | Podaima | 604/67 |

* cited by examiner

*Primary Examiner* — Matthew F Desanto
(74) *Attorney, Agent, or Firm* — Wang Law Firm, Inc.

(57) ABSTRACT

A system for safe delivery of drug to a patient employs a programmable memory card for transferring drug delivery instructions and patient information between a server in a pharmacy and a drug delivery apparatus in a patient room. The server in the pharmacy checks the prescription for safety and the drug delivery apparatus checks for the drug delivery instructions and also the patient identity. The drug delivery apparatus records the information about the drug delivered to the patient onto the programmable memory card at the end of the drug delivery.

15 Claims, 7 Drawing Sheets

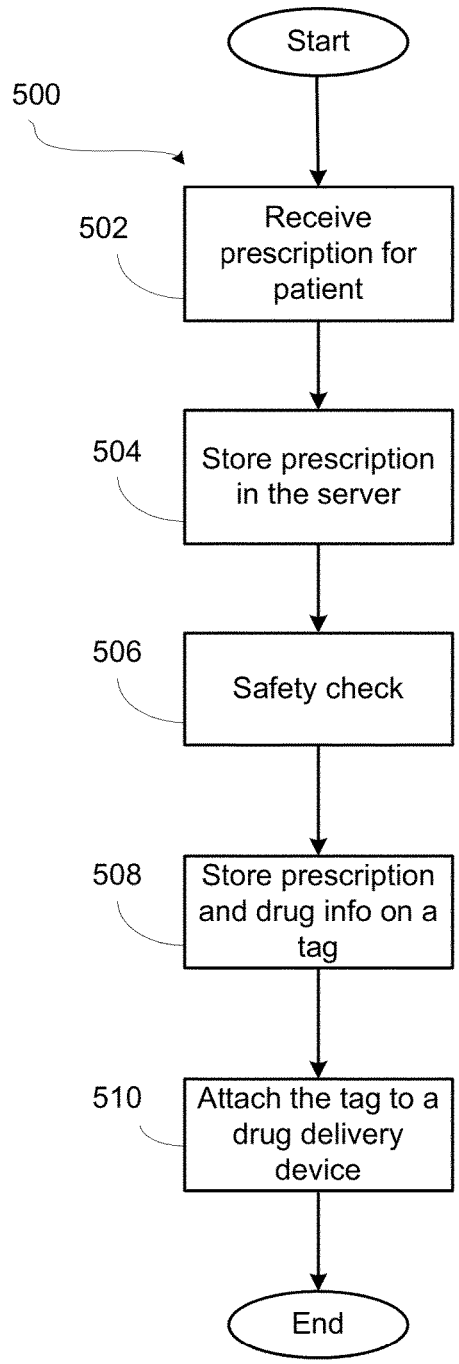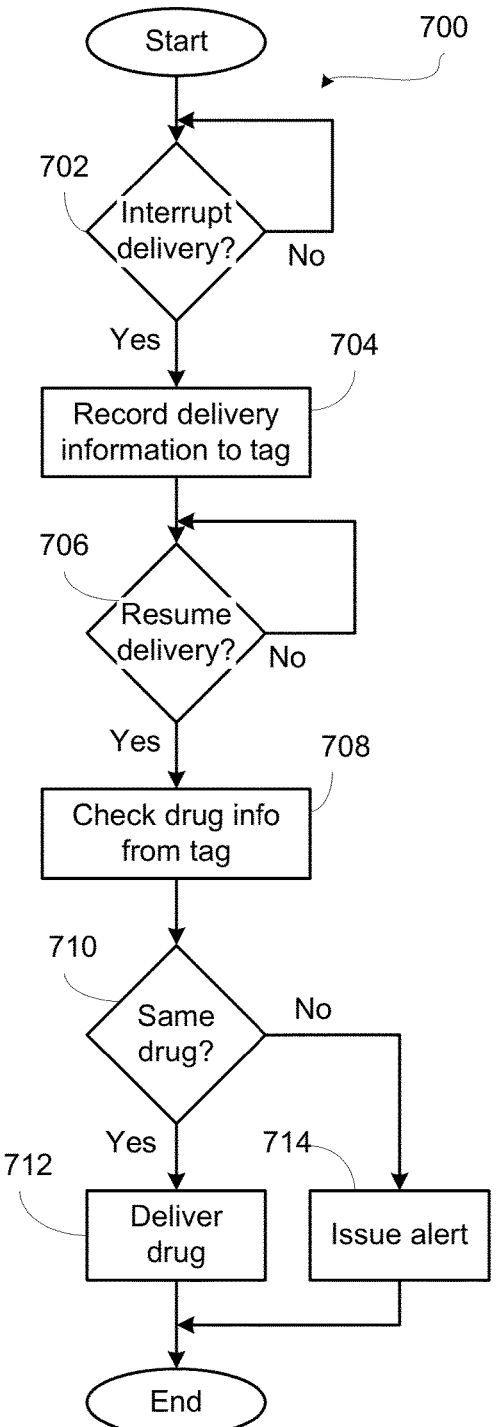
Fig. 5
Fig. 7

SAFE DRUG DELIVERY SYSTEM

FIELD OF THE INVENTION

The invention relates to pharmaceutical drug delivery, and more particularly, to a system for safe drug delivery.

BACKGROUND OF THE INVENTION

To reduce the potential for errors in drug infusion, current advanced infusion pumps store a drug library that sets soft and hard limits for the range of the infusion parameters, such as infusion rate, bolus, and total bolus. The health care professional (HCP), e.g., doctor, nurse, or pharmacist, can override the soft limit, but not the hard limit. The drug infusion history is recorded by the pump to be retrieved for post-surveillance or accounting purposes.

There are several problems with the current system. One problem is that the drug library is stored in the pump without the benefit of patient data. The limits of the parameters must be wide enough to account for the variation among individual patients within the population. However, these limits in some cases may still be too wide to prevent unsafe dosing for an individual patient. Another problem is that the same drug can have different concentrations and limits depending on the hospital environment (e.g., NICU, PICU, ICU, OR, etc). The HCP must manually select the correct entry from the drug library and a wrong selection can result in the wrong concentration, infusion mode, or limits thus resulting in delivery errors. Currently available pumps cannot effectively check drug delivery information against patient identification information. This allows the possibility of errors such as the wrong drug being infused to the wrong patient and patient weight information being wrongly entered manually, which can result in an incorrect infusion rate for body weight mode infusion. Maintenance of drug libraries throughout an institution's pump inventory is another problem. The drug library stored in the pump must be electronically updated (manually or wirelessly) and the task is more difficult when pumps are distributed across multiple locations within the institution. Finally, current methods for capturing actual drug infusion history are not very convenient for the purpose of surveillance or accounting. Manual downloading of infusion history from the pump is labor-intensive. The use of wireless networking to transmit infusion history records is another method; however, the wireless network at a hospital can be unreliable, and troubleshooting often requires technical expertise not available to the HCP using the pump.

Therefore, there is a need for a system that safely and conveniently delivers drugs using infusion pumps to patients, and it is to this apparatus the present invention is primarily directed.

SUMMARY OF THE INVENTION

The present invention provides a system and method for safely delivering drugs to patients and also for tracking the drug delivery to each patient. The method includes retrieving, from a programmable memory card, drug, and patient information as well as the drug delivery instructions, forming a retrieved drug delivery parameters, comparing, at a drug delivery device, the retrieved drug delivery parameters with a stored information in the drug delivery device, issuing an alert if the stored information is different from the retrieved drug delivery parameters, overriding pump default operational options (alarm settings such as near empty time, occlusion force level, and the audio type/volume etc.), and recording, by the drug delivery device, drug delivery data on the programmable memory card.

In another embodiment, the invention provides another method that includes checking received prescription information against information stored in a drug library on a server or computer, issuing an alarm if the received prescription information is outside the allowable range in the drug library, and storing, by a card interface, drug information and patient information retrieved from a server in a programmable memory card, the drug information including the prescription information.

In yet another embodiment, the invention provides an apparatus that a memory card interface for retrieving drug delivery instruction, patient information, and adjusted pump default parameters from a memory card and for storing drug delivery data onto the memory card, a non-transitory computer readable storage unit for storing drug delivery instructions, a controller for checking the patient information, converting drug delivery instructions into infusion parameters, and adjusting pump internal defaults, and a drug delivery mechanism for delivering drug to a patient according to the drug infusion parameters.

BRIEF DESCRIPTION OF THE DRAWINGS

Features and advantages of embodiments of the invention will become apparent as the following Detailed Description proceeds, and upon reference to the Drawings, where like numerals depict like elements, and in which:

FIG. 5 is a flowchart for programming a programmable memory card;

FIG. 7 is a flowchart for interrupting and resuming drug delivery;

DETAILED DESCRIPTION OF THE INVENTION

Figure 1:
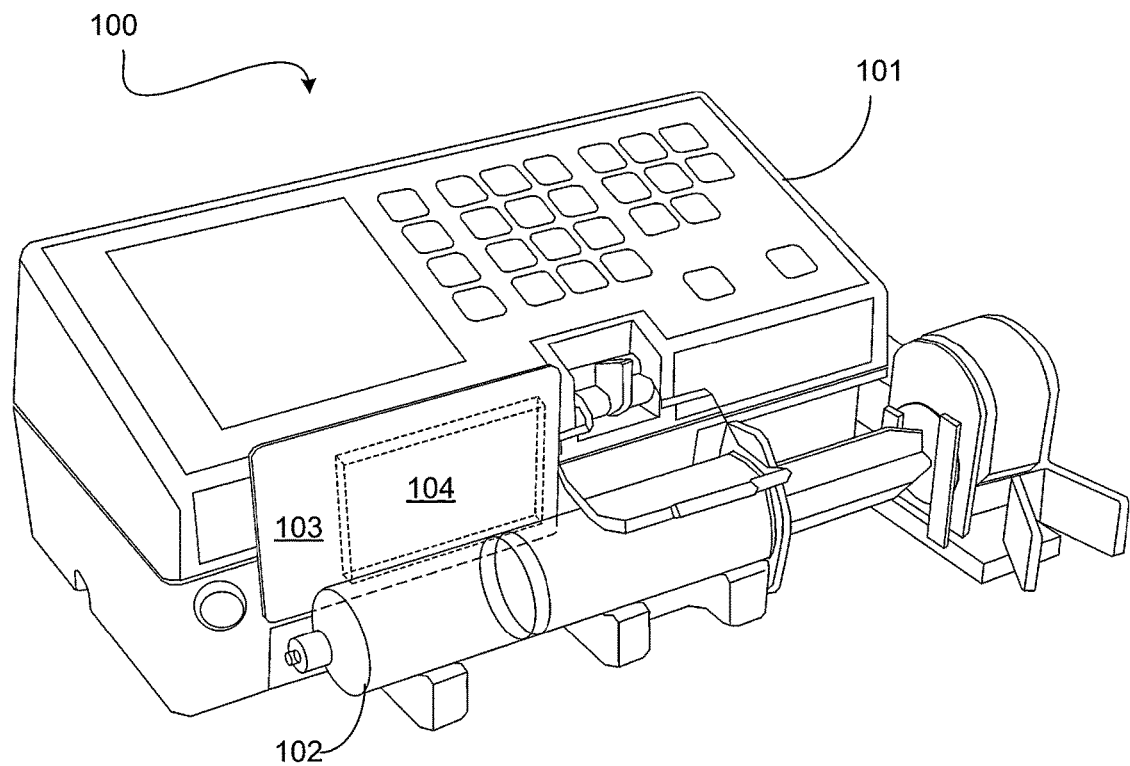
FIG. 1 illustrates a schematic view of an infusion pump with a syringe for safe drug delivery according to one embodiment of the invention.

The present invention provides a system and method for delivering drugs safely. The invention consists of using a programmable read/write memory card associated with a drug delivery container (e.g. syringe or bag) filled with an infusate (e.g. drug, fluid, nutrient, blood product, etc.) to be dispensed to a patient. The read/write card contains information pertinent to the infusate, such as drug name, concentration, infusion rate, adjustable limits of parameters, syringe model, capacity, viscosity, etc. The read/write card can also contain information about the patient, such as patient identification number, date of birth, vital statistics, patient history, allergy information, etc. Furthermore, the read/write card is capable of keeping a record of operations and changes.

The read/write card (e.g. RFID tag or magnetic memory strip) is initially programmed at a control station (e.g. pharmacy, nursing area, central drug database) with all of the necessary operational instructions. The instructions include all medical delivery parameters, patient data, and parameters for the operation of the syringe pump. The control station can determine what parameters to program into the read/write card. A visual readable label containing all of the above information is printed and placed on the programmable card for visual inspection or verification. The card is then attached to the drug container, which may be double-checked and recorded by a different individual to ensure information accuracy in accordance with the institution's policies. The package is delivered to the patient's residence (e.g. patient's room, emergency room, operating room, etc.). Once mounted onto the pump, the card is automatically detected and read by the infusion pump. The infusion pump proceeds to check the patient's ID information against the current ID stored within the infusion pump, or prompts the health care professional to enter a valid patient ID. The infusion pump automatically downloads all the instructions from the card into the infusion pump's internal memory. The pump will start delivery using the infusion parameters tailored to the patient's specific medical needs, thus reducing the labor burden on the health care professional to make major manual selection and adjustments. These parameters may be altered within the hard limits by the health care professional. The health care professional will be optionally prompted to enter his or her ID information and confirm the pump settings.

During drug delivery, the infusion rate may be adjusted or the drug delivery may be interrupted. The infusion pump will record the status of the drug delivery onto the card should these events occur. The pump will also retain this information in its internal history files. The card and the drug container can be returned to the processing center once drug infusion is completed, where the data on the card can be retrieved for patient medical record storage, post-surveillance, or accounting. The card may contain additional data such as the serial number of the pump or Health Professional ID, and any operational adjustments made by the pump or the health care professional.

The advantage of this system is that it facilitates infusion pump programming on site by a qualified health care professional, and utilizing information that is pre-programmed and verified at a pharmacy or central drug database under a more controlled environment. It also removes the need to maintain an up-to-date drug library inside each infusion pump. Architecturally, the card and pump can therefore operate without connecting to a central computer system or receiving instructions from a central database. Multiple safety redundancies within the system lessen the chance of unsafe operation which may jeopardize the health of a patient.

FIG. 1 illustrates in general a schematic view 100 of an infusion pump 101 with a syringe 102 for safe drug delivery according to one embodiment of the invention. The syringe 102 is attached to a programmable memory card 103 and the infusion pump 101 is equipped with a memory card interface 104. The memory card interface 104 is capable of retrieving the data stored in the programmable card 103. The memory card interface 104 is also capable of storing data to the programmable card 103. The infusion pump 101 has a set of default operational options that can be adjusted by a HCP to customize the infusion pump 101 for a particular patient and a particular use condition. The operational options includes, among others, the occlusion force level, the option to enable bolus delivery, the option to set a delivery limit, and the options for alarm setting, alarm type, and alarm volume. The default operational options may be adjusted by the HCP and may also be overridden by the drug delivery instructions in the programmable memory card 103. The pump default operational options in the drug delivery instructions may be programmed according to library instructions or hospital policy to meet the need of a particular drug or the patient.

Figure 2:
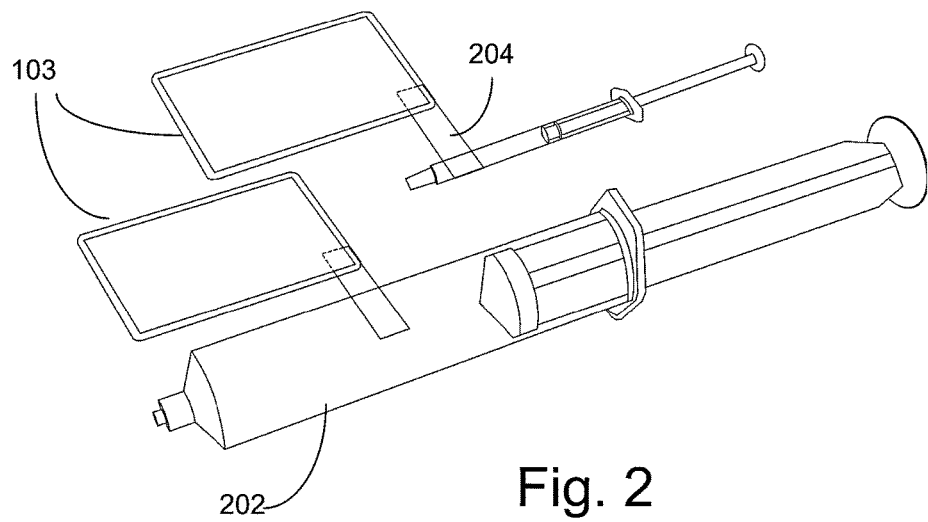
FIG. 2 illustrates various syringes and sizes with programmable memory cards.

FIG. 2 illustrates various syringes with programmable memory cards 103. The memory card 103 can be attached to the body 202 of the syringe by means of a connecting device 204. A printed visually readable label with drug information and patient information is placed on the memory card 103, so it is easy for a HCP to inspect. The connecting device 204 may be an adhesive tape or other attaching means. Alternatively, the memory card 103 can be disposed on the body 202 of the syringe directly if the relative sizes of the memory card 103 to the syringe 102 permit or if the memory card 103 is flexible.

Figure 3:
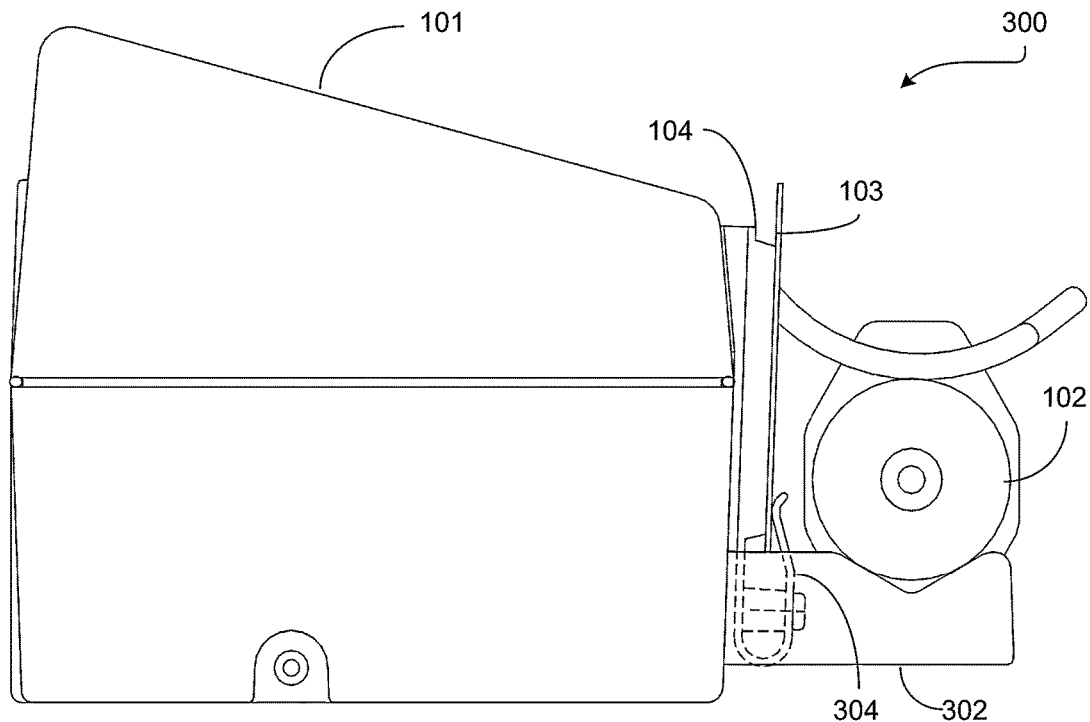
FIG. 3 illustrates a side view of an infusion pump with a programmable memory card.

FIG. 3 illustrates a side view 300 of a syringe 102 mounted on an infusion pump 101. The memory card 103 is preferably attached on the side of the syringe body 202 such that it can be easily read by the memory card interface 104 built into the infusion pump 101. The memory card interface 104 is a RFID card reader/writer and is preferably disposed near the saddle 302 that holds the syringe 102, so the memory card interface 104 can read the memory card 103 easily. The memory card 103 has a non-volatile, non-transitory, and computer readable memory for storing information. The memory card 103 may be a programmable RFID (radio-frequency identification) card and its content can be detected and read by the memory card interface 104 wirelessly when the memory card 103 is moved closer to the memory card interface 104. The memory card 103 may be either a passive RFID card (without power source) or an active RFID card (with a power source). Alternatively, the memory card 103 may have a magnetic strip (similar to a traditional credit card) where the information is stored and the memory card interface 104 is a magnetic card reader/writer (similar to the card reader used to read a traditional credit card). The infusion pump 101 is capable of writing to the memory card through the memory card interface 104. The memory card interface 104 is capable of storing the information into the memory card 103 wirelessly through radio signals. If the memory card interface 104 is a magnetic card reader/writer, the storing of information into the memory card 103 is done by swiping the memory card 103 through the magnetic card reader when prompted by the magnetic card reader. The memory card interface 104 is equipped with a card holder 304, which can be a simple clip, where the memory card 103 can be inserted and held, such that the infusion pump 101 can be mounted in different positions and the memory card 103 will not dislodged from the proximity of the memory card interface 104.

Figure 4:
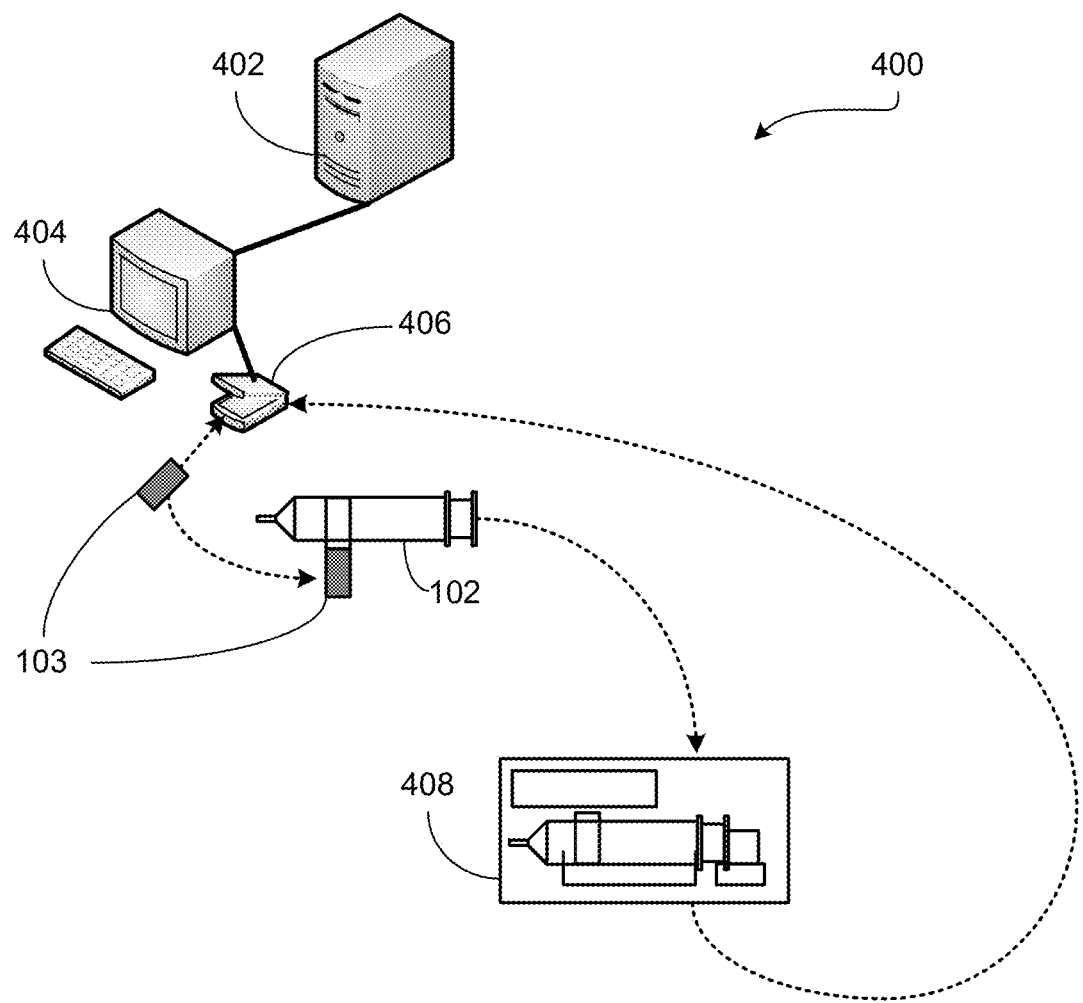
FIG. 4 illustrates a system for drug identification and delivery according to an embodiment of the invention.

FIG. 4 illustrates a safe drug delivery system 400. The safe drug delivery system 400 includes a server 402, a user terminal 404, a card interface 406 attached to the user terminal 404, a syringe 102 with a memory card 103, and a drug delivery apparatus 408. A database (a drug library) with drug information and patient information resides in the server 402. The information in the database is used to program the memory card 103 and the programming is done by means of the user terminal 404 and the card interface 406. The server 402, the user terminal 404, and the card interface 406 are typically setup in a pharmacy in a hospital, or other health care providing facility, and accessed by a pharmacist. The card interface 406, though shown in FIG. 4 as a unit separated from the server 402, can be an integral part of the server 402 or the terminal 404. The user terminal 404 may be local to the server 402 and may also be located remotely from the server 402. The drug delivery apparatus 408 is typically an infusion pump 101 setup at the drug delivery point, which can be a patient room, an intensive care unit, or an operating room. The drug delivery apparatus 408 may also be an intelligent intravenous therapy (IV) apparatus, which is an IV apparatus with a card reader and a delivery controller. The pharmacist, at the user terminal 404, retrieves the patient information and drug information from the database and enters the delivery information according to the prescription received from a physician. The server 402 performs drug delivery safety checking, which includes checking the delivery information for the prescribed drug against the drug information to make sure that the drug delivery is not exceeding any limit set by either the hospital or the manufacturer. The drug delivery safety checking also checks the drug against patient's known allergy or adverse interaction between the drug to be delivered and other drugs that have been administrated to the patient. After checking for drug delivery safety, the server 402 will prompt the user (pharmacist) to insert the memory card 103 into the card interface 406 and the memory card 103 will be programmed with delivery instructions. The delivery instructions are preferably encrypted, so that the patient privacy information can be protected.

After being programmed, the memory card 103 is attached to a syringe 102, which will be delivered to a drug delivery apparatus 408. A print label may also be produced by a printer (not shown) attached to the server 402 for attaching to the memory card 103. The delivery instructions will be retrieved and decrypted by the drug delivery apparatus 408 and the delivery instructions are used to derive the drug delivery parameters on the drug delivery apparatus 408. The drug delivery parameters include, for example, the speed and time interval of motor operation to obtain the desired drug delivery rate and drug dose. Once drug delivery has completed, the drug delivery apparatus 408 will record drug delivery data to the memory card 103 and also will keep a copy of the drug delivery data in the memory inside the drug delivery apparatus 408 as backup. The syringe 102 is disconnected from the drug delivery apparatus 408 and the memory card 103 along with the syringe 102 are returned to the pharmacy or a central processing department, where the memory card 103 is read by the card interface 406 and the syringe 102 discarded. The information on the memory card 103 is read for post-delivery recordation and analysis. The information is uploaded to the database for storage and also for accounting or other purposes. Alternatively, the memory card 103 can be detached from the syringe 102 and returned to the pharmacy or the central processing department, while the syringe 102 is discarded at the end of the drug delivery.

FIG. 5 illustrates a flowchart 500 for programming a programmable memory card 103. A qualified healthcare professional prescribes medication for a patient and the prescription is input to the server 402, step 502. The prescription data, which includes delivery instructions, is stored in a non-transitory, computer readable memory in the server 402, step 504. The server 402 performs a safety check for consistency with internal safety constraints, step 506. The safety check consists of checking the prescription data against the information stored in the drug library. The safety constraints may include the soft and hard drug dose limits. Both the hard and soft drug dose limits may be set by the drug manufacturer, Federal Drug Administration (FDA), hospital, or qualified medical professionals. The safety check further consists of checking the prescription data against the patient's medical history for allergic reactions or complications arising from incompatible drug dosages within a short window of time. If the prescription is incompatible with information in the drug library, i.e., if the prescribed drug dose does not fall within pre-defined safety dose limits set by the hospital or the drug manufacturer, or is found to likely cause adverse reactions, the server 402 issues an alarm or a warning to a technician or pharmacist. The pharmacist may override the alarm or modify the prescribed drug dose after consulting with the issuing physician. Once the prescription has passed the safety check, the server 402 writes the drug delivery instructions, which includes the prescription information, patient information, and any relevant delivery information, onto the programmable memory card 103, step 508, and prints a readable label to be applied to the memory card. The memory card 103 may then be attached to a drug delivery device 102, step 510, for operation in accordance with the delivery instructions.

Figure 6:
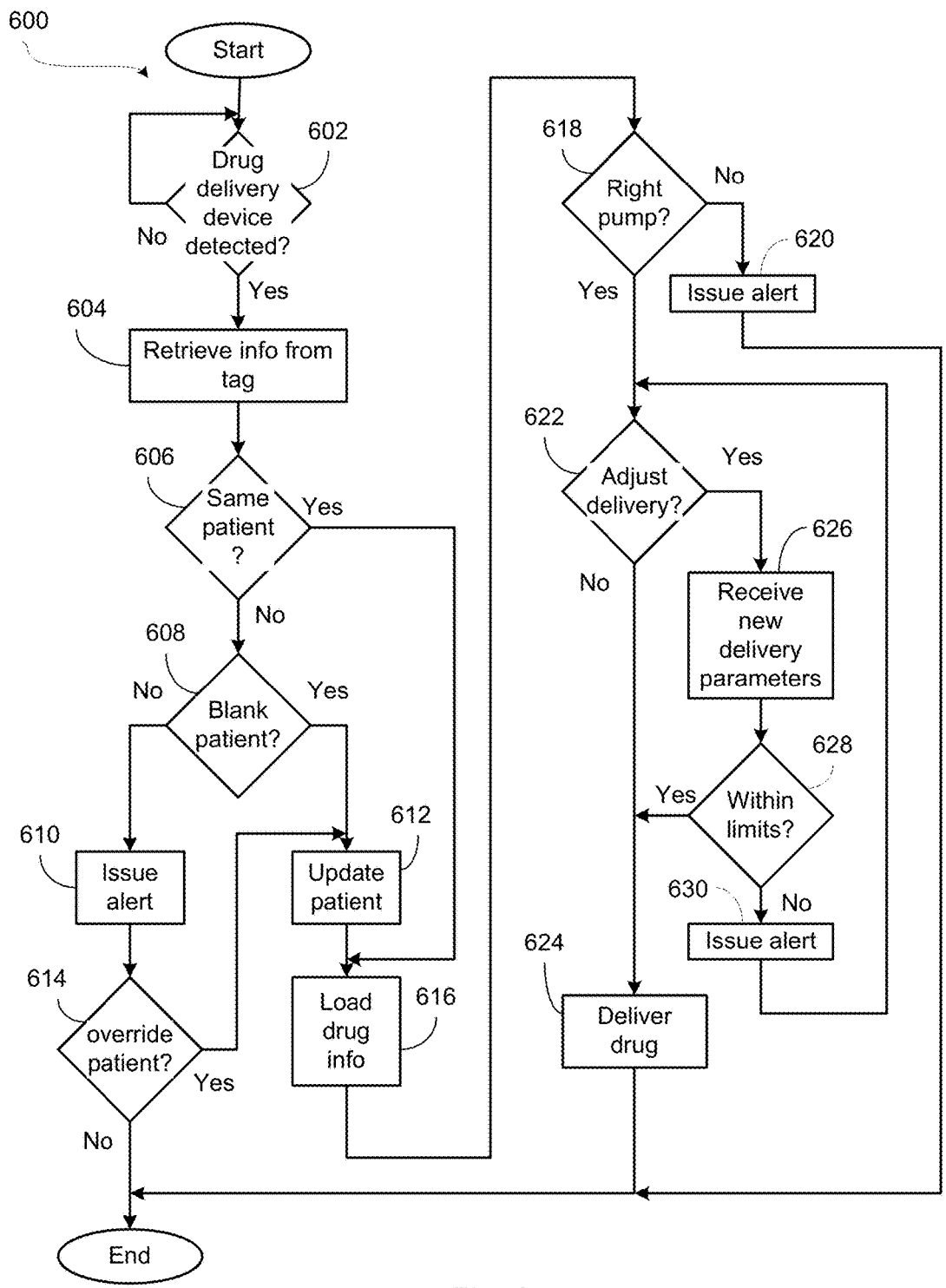
FIG. 6 is a flowchart for delivering drugs according to one embodiment of the present invention.

FIG. 6 is a flowchart 600 illustrating the drug delivery according to the invention. The infusion pump 101 attempts to detect the presence of a drug delivery device, which is a syringe 102, step 602. The presence of the syringe 102 is detected when the programmable memory card 103 is close to a memory card interface 104 and the syringe is placed on the saddle 302 of an infusion pump 101. Once detected, the infusion pump 101 reads the drug delivery instructions from the programmable memory card 103, step 604. The drug delivery instructions include patient identity. The infusion pump 101 then performs a consistency check by comparing the patient identity from the memory card 103 to the patient identity currently stored in the infusion pump's memory, step 606. If the patient identity in the programmable memory card 103 does not match the patient identity on the infusion pump 101, the infusion pump 101 will check if the infusion pump 101 is not assigned to any patient yet (blank patient information), step 608. If the infusion pump 101 does have the patient identity and the patient identity is different from the patent data from the programmable memory card 103, the infusion pump 101 will issue an alert, step 610. At this point, the HCP has the option of overriding the patient identity, step 614, and to update the patient information in the infusion pump 101, step 612. Updating the patient information will modify the patient identity in the infusion pump 101 with the patient identity from the programmable memory card 103. If the syringe 103 is delivered incorrectly to a different hospital room, then the HCP should not confirm the patient information or update the patient information in the infusion pump 101.

If the patient data in the programmable memory card 103 does match the patient information on the infusion pump 101, the infusion pump 101 will load the drug delivery instructions from the programmable memory card 103, step 616. The same operation for loading the drug delivery instructions will also be executed by the infusion pump 101 if the HCP updates the patient information on the infusion pump 101, step 612, with the patent data from the programmable memory card 103.

Once the drug delivery instructions are read from the memory card 103, the infusion pump 101 performs a further consistency check to determine whether the infusion pump 101 is mechanically capable of delivering the drug according to the drug delivery instructions, step 618. The consistency check includes checking default operational options of the infusion pump 101 against the drug delivery parameters in the memory card 103. The capacity of the infusion pump 101 may be smaller than what is needed to deliver the drug. If the infusion pump 101 is not the right pump, the infusion pump 101 will issue an alert, step 620, then stops. If the infusion pump 101 is capable of delivering the drug, the HCP is offered the chance to adjust the delivery parameters, step 622. This adjustment of delivery allows a HCP to adjust the drug delivery rate according to the patient's condition and this adjustment is useful if the infusion pump 101, or other type of delivery system, is used in an operating room or used under a condition when the patient's condition changes relatively quickly in a short period of time. The drug delivery rate is input by a HCP and received by the infusion pump 101. This received drug delivery rate overrides the drug delivery rate in the drug delivery instructions retrieved from the programmable memory card 103. If no adjustment is done, the infusion pump 101 proceeds to administer the drug according to the drug delivery parameters derived from the drug delivery instructions, step 624. If an adjustment of the delivery parameters is made, the infusion pump 101 receives the new delivery parameters, step 626, and checks whether the received new delivery parameters are within the safe limits, step 628. If the drug delivery parameters are not within limits, the infusion pump 101 issues an alert, step 630, and awaits further adjustment by an HCP, step 622. If the new delivery parameters are within the safe limits, the delivery is started, step 624. Optionally, the infusion pump 101 may prompt the HCP to enter his or her identity. Besides the drug delivery parameters, the infusion pump operational options may also be modified by the HCP according to the specific delivery condition for the patient.

FIG. 7 is a flowchart 700 that illustrates interruption of drug delivery and subsequent resumption of drug delivery using a drug infusion pump 101. After the syringe 103 is mounted on the infusion pump 101 and the drug delivery started, the infusion pump 101 checks whether the drug delivery is interrupted, step 702. The infusion pump 101 tracks the drug delivered by the infusion pump 101. The drug delivery can be interrupted for a variety of reasons, such as initiated by an HCP or caused by some problem with the infusion pump 101. For example, the drug delivery may be temporarily stopped to allow respiratory treatment, or the pump may malfunction, in which case the drug will be delivered by other pump. When the drug delivery is interrupted, the infusion pump 101 will record the drug delivery data executed up until the interruption, step 704. The data may include the amount of drug delivered, the drug delivery rate, and the identity of the HCP who administrated the drug. The drug delivery rate may be different from the original drug delivery rate set by the pharmacy because of the possibility of adjustment by the HCP. If a resume operation command is given to the infusion pump 101, the infusion pump 101 reads the drug delivery data in the memory card 103, step 708, and determines if the drug delivery data is the same as the delivery data stored inside the infusion pump 101, step 710. If the infusion pump 101 detects inconsistencies in drug delivery data (such as different drug type, altered delivery rate, change in dosage, or different patient ID), the pump 101 issues an alert, step 714, and halts delivery. A nurse or technician may correct the delivery parameters as necessary, or may manually override the alert. If no problem is detected, the infusion pump 101 then proceeds to deliver the drug, step 712. If the programmable memory card 103 is removed from the proximity of the infusion pump 101, the infusion pump 101 will stop the drug delivery and issue an alarm. When the programmable memory card 103 is returned to the infusion pump 101, the infusion pump 101 will resume the drug delivery after a safety check. The infusion pump 101 will allow an HCP to override any alarm and to force the drug delivery even if the programmable memory card 103 is removed.

When a drug delivery is interrupted because of a problem in the infusion pump 101, the drug delivery may be resumed by moving the syringe 102 to a replacement infusion pump. The replacement infusion pump 101 will perform steps described in FIG. 6, except that the drug delivery data previously stored by the previously infusion pump 101 is used.

Figure 8:
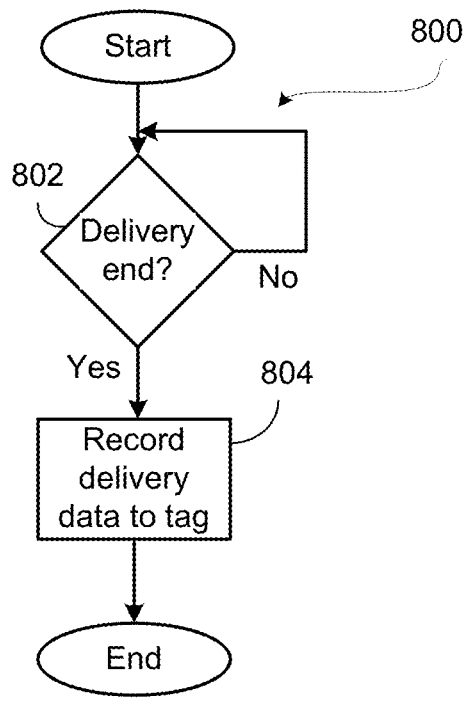
FIG. 8 is a flowchart illustrating the end of drug delivery.

FIG. 8 is a flowchart 800 illustrating the end of drug delivery. The infusion pump 101 continues to monitor the delivery of drug, step 802. When the drug delivery ends, the infusion pump 101 will record the drug delivery data regarding the drug delivery to the programmable memory card 103, step 804. Drug delivery data may include, but is not limited to: the dosage volume of the drug, the time stamps of delivery start and end, the instantaneous delivery parameters, the type of drug, the identity of the HCP who performed the delivery, the identity of the physician who authorized the delivery, any record of errors or unexpected operation, or the volume of any remaining undelivered dosage. Once the infusion pump 101 writes the drug delivery data to the memory card 103, the memory card 103 and the drug syringe 102 can be safely removed from the infusion pump 101 without triggering any further alerts.

Figure 9:
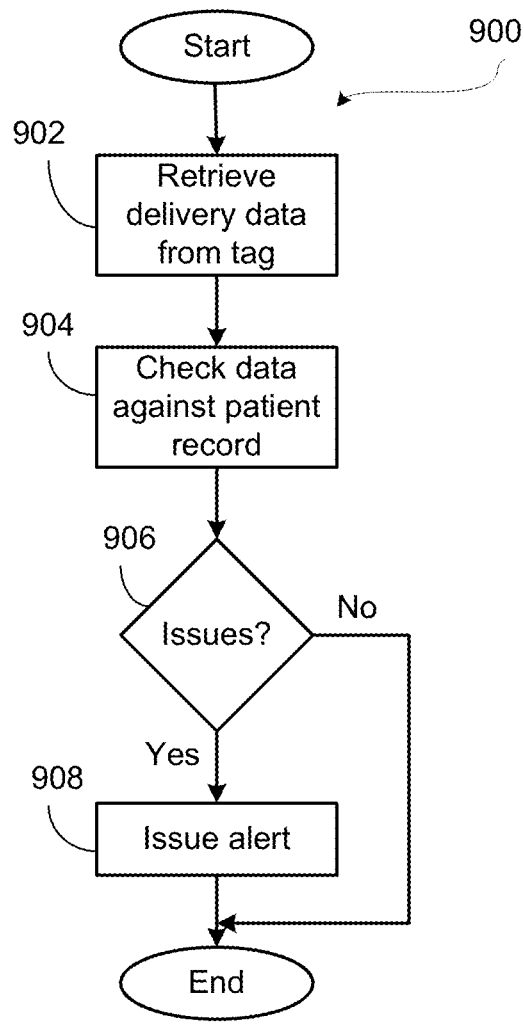
FIG. 9 is a flowchart for retrieving information from a programmable memory card.

FIG. 9 is a flowchart 900 depicting how the read/write memory card 103 is read when returned to the pharmacy or central processing department. After the drug is delivered, the empty syringe 102 and the programmable memory card 103 are removed from the infusion pump 101 and returned to the pharmacy or accounting department. The card interface 406 reads the memory card 103 to retrieve relevant drug delivery data recorded by the infusion pump 101, step 902, and the drug delivery data is sent to the server 402. The server 402 stores the drug delivery data read by the card interface 406. The server 402 may also perform an internal consistency check by reviewing the drug delivery data recorded by the infusion pump 101 against previously stored patient data, step 904. The consistency check includes checking the amount of drug actually delivered to the patient against the amount of drug prescribed by the physician, which is stored in the driver 402. The consistency check may also check the actual drug delivery rate against the drug delivery rate prescribed by the physician. If inconsistencies are found, step 906, such as the amount of the drug delivered being different from the amount of drug prescribed by the physician, then the server 402 may issue one or more alerts, step 908. The server 402 may be capable of sorting or prioritizing the alerts in order of their severity.

Figure 10:
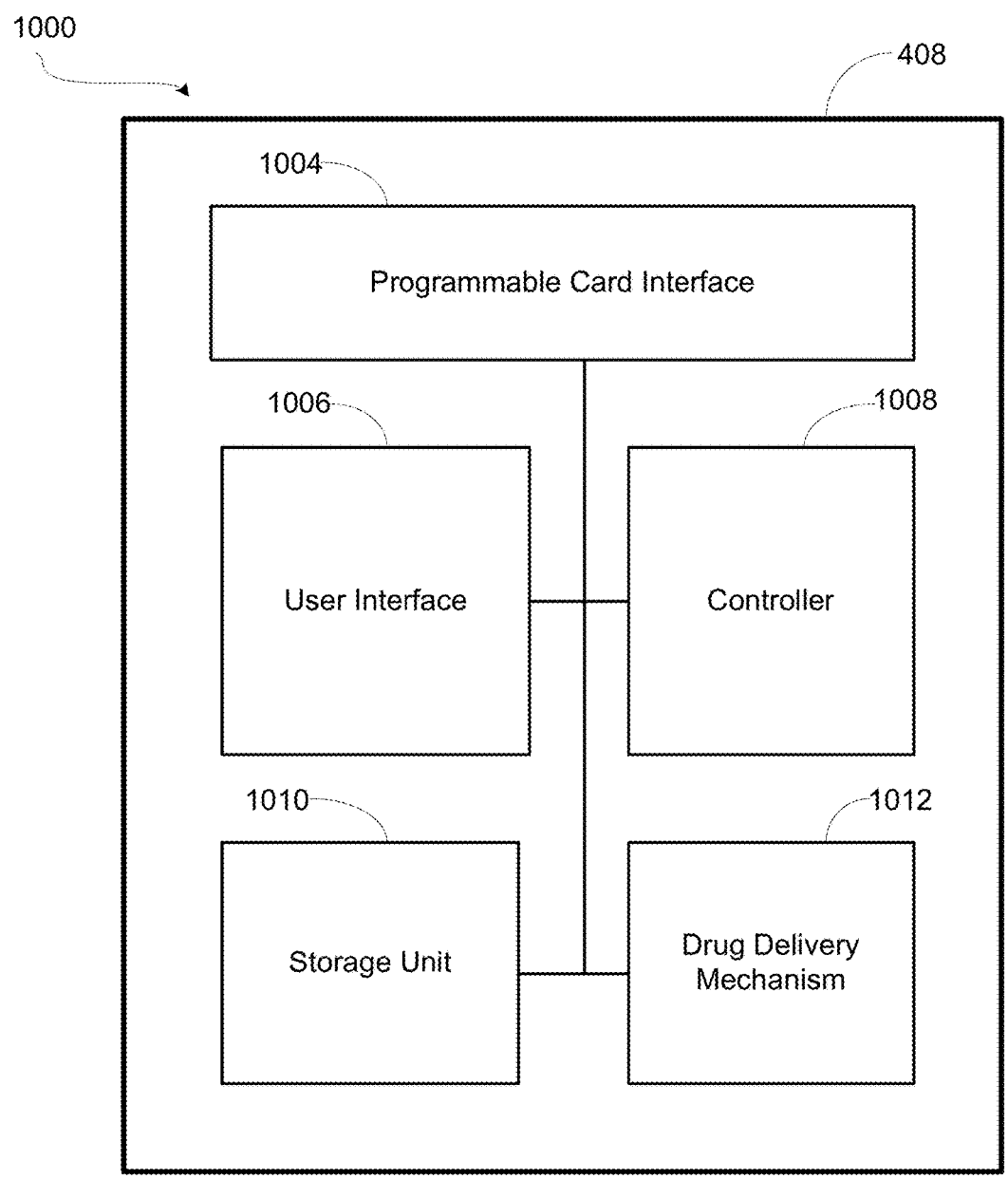
FIG. 10 depicts architecture of a drug delivery device.

FIG. 10 depicts architecture 1000 of a drug delivery apparatus 408. The drug delivery apparatus 408 has a programmable card interface 1004, a user interface 1006, a controller 1008, a storage unit 1010, and a drug delivery mechanism 1012. The programmable card reader interface 1004 interfaces with the memory card interface 104 and receives drug delivery instructions from the programmable memory card 103. The user interface 1006 interfaces with input and output devices, including sending the drug information to a display device (not shown). The storage unit 1010 is a non-transitory computer readable memory and stores patient information, and drug delivery data. The drug delivery mechanism 1012 controls the delivery of drug in the syringe pump. The controller 1008 controls the operation of the drug delivery apparatus 408, including checking the drug delivery instructions against the drug delivery data in the storage unit 1010 and tracking the drug delivered by the drug delivery apparatus 408.

In operation, when a patient is hospitalized, a physician usually prescribes some drug to be administered during his/her stay. The drug usually is administered parenterally. The drug prescription is delivered to the hospital's pharmacy department. The drug prescription is entered into a server in the pharmacy and the server checks the drug information in the drug prescription against the drug library and also against the patient's own history. The server may check against any drug allergy that the patient may have or dangerous drug interactions for this particular drug. The pump default operational options may be adjusted such as near empty time or occlusion level to meet the need of a particular drug or the patient. After this safety check, the server 402 will generate drug delivery instructions, which include patient identity and drug delivery parameters, and store the drug delivery instructions onto a programmable memory card 103 through a card interface 406 and print a corresponding label to be applied to the memory card.

The programmable memory card 103 is attached to a syringe 102 and the syringe 102 is delivered to the patient's room. The syringe 102 is placed on an infusion pump 101 through which the drug is delivered to the patient. The infusion pump 101 will detect the programmable memory card 103 once the card is properly loaded and download the drug information from the programmable memory card 103. The infusion pump 101 will check the patient identity from the programmable memory card 103 to make sure that the syringe 102 is delivered to the correct patient. The infusion pump 101 will allow adjustment of the drug delivery parameters. The drug delivery parameters can be adjusted at the point of delivery and this allows flexibility for a physician to adjust the drug dose according to the patient's condition.

During the drug delivery, the infusion pump 101 continuously checks the delivery operation and presence of the syringe 102. If the drug delivery is interrupted for any reason, the infusion pump 101 will record the data about the drug delivered so far in the programmable memory card 103. This information will be checked for safety by the infusion pump 101 when the drug delivery is resumed. When the drug delivery is complete, the infusion pump 101 will record the drug delivery data back onto the programmable memory card 103. The programmable memory card 103 is returned to the pharmacy or central processing department with or without the empty syringe 102. The data on the programmable memory card 103 is read and the drug delivery information, amount and rate, is stored in the server 402. The drug delivery data may also be sent to the accounting department for billing purposes or post surveillances of drug usage.

The terms and expressions which have been employed herein are used as terms of description and not of limitation, and there is no intention, in the use of such terms and expressions, of excluding any equivalents of the features shown and described (or portions thereof), and it is recognized that various modifications are possible within the scope of the claims. Other modifications, variations, and alternatives are also possible. Accordingly, the claims are intended to cover all such equivalents. Dimensions in the drawings here presented are not to scale unless otherwise indicated. It is recognized that different features and steps depicted in different figures and described in different scenarios maybe combined or interchanged. Drug delivery is used to describe the general process of dispensing infusate to a patient and not limited to the delivery of medicine only.

What is claimed is:

1. A method, for safe drug delivery, comprising the steps of:
    retrieving wirelessly, from a programmable memory card attached to a drug container, a patient identity, forming a retrieved patient identity, and drug delivery parameters, forming the retrieved drug delivery parameters;
    comparing, at a drug delivery device, the retrieved patient identity with a stored patient identity in the drug delivery device;
    issuing an alert if the stored patient identity is different from the retrieved patient identity;
    checking operational options of the drug delivery device against the retrieved drug delivery parameters to determine if the operational options of the drug delivery device is capable of delivering the drug according to the retrieved drug delivery parameters;
    issuing an alert if the drug delivery device is incapable of delivering the drug according to the retrieved drug delivery parameters;
    delivering, by the drug delivery device, a drug in the drug container to a patient according to the retrieved drug delivery parameters;
    detecting wirelessly, by the drug delivery device, the programmable memory card is removed;
    stopping delivery of the drug in the drug container to the patient if the programmable memory card is removed; and
    recording wirelessly, by the drug delivery device, drug delivery data in the programmable memory card, wherein
    the drug delivery data comprises type of drug, amount of drug delivered, drug delivery rate, and time of drug delivered and the drug delivery data are sent for recording via the programmable memory card.

2. The method of claim 1, further comprising the steps of:
    receiving, at the drug delivery device, a drug delivery parameter, forming a received drug delivery parameter; and
    overriding at least one retrieved drug delivery parameter with the received drug delivery parameter.

3. The method of claim 2, further comprising the step of overriding default operational options in the drug delivery device with options in the retrieved drug delivery parameters.

4. The method of claim 2, further comprising the steps of:
    checking the received drug delivery parameters against a set of safe limits; and
    issuing an alert if at least one received drug delivery parameter is outside of the set of safe limits.

5. The method of claim 1, further comprising the step of
    if the retried patient identity is different from the stored patient identity, updating the stored patient identity with the retrieved patient identity; and
    enabling the drug delivery device to be used for a patient identified by the retrieved patient identity.

6. The method of claim 1, further comprising the steps of:
    interrupting drug delivery by the drug delivery device; and
    before resuming the drug delivery, retrieving a patient identity from the programmable memory card and comparing the retrieved patient identity with the stored patient identity.

7. The method of claim 1, wherein the step of checking operational options of the drug delivery device against the retrieved drug delivery parameters further comprising the step of checking if a capacity of the drug delivery device pump is smaller than a capacity needed for safe drug delivery.

8. A safe drug delivery apparatus comprising:
a memory card interface retrieving a first patient identity and drug delivery instructions from a memory card attached to a drug container and storing drug delivery data onto the memory card;
a non-transitory computer readable storage unit storing a second patient identity and the drug delivery instructions and drug delivery parameters derived from the drug delivery instructions;
a drug delivery mechanism configured to deliver a drug to a patient according to the drug delivery parameters; and
a controller checking the second patient identity in the non-transitory computer readable storage unit against the first patient identity and checking operational options of the safe drug delivery apparatus against the drug delivery parameters to determine if the operational options of the safe drug delivery apparatus is capable of delivering the drug according to the drug delivery parameters, the controller being capable of overriding the second patient identity in the non-transitory computer readable storage unit with the first patient identity, wherein the controller stops delivery of the drug in the drug container to the patient if the memory card is removed;
wherein
the drug delivery data comprises type of drug, amount of drug delivered by the drug delivery mechanism, drug delivery rate, and time of drug delivered, and the safe drug delivery apparatus records the drug delivery data to the memory card for external recording purpose.

9. The safe drug delivery apparatus of claim 8, further comprising a user interface for receiving a drug delivery dose from a user, wherein the controller overrides a prescribed drug delivery dose in the drug delivery instructions with the drug delivery dose received through the user interface.

10. The safe drug delivery apparatus of claim 8, wherein the controller issues an alert if the second patient identity is different from the first patient identity.

11. The safe drug delivery apparatus of claim 8, wherein the memory card interface is a radio frequency identification card reader and writer.

12. The safe drug delivery apparatus of claim 8, wherein the memory card interface is a magnetic card reader and writer.

13. The safe drug delivery apparatus of claim 8, wherein the controller can interrupt drug delivery by the drug delivery mechanism and stores drug delivery data onto the memory card.

14. The safe drug delivery apparatus of claim 8, wherein the controller checks the patient identity retrieved from the memory card against the patient identity stored in the non-transitory computer readable storage unit before resuming drug delivery.

15. The safe drug delivery apparatus of claim 8, wherein the controller checks if a capacity of the safe drug delivery apparatus is smaller than a capacity needed for safe drug delivery.

* * * * *